United States Patent [19]

Ball et al.

[11] Patent Number: 4,497,969

[45] Date of Patent: Feb. 5, 1985

[54] PROCESS FOR THE PRODUCTION OF CATALYSTS BASED ON CRYSTALLINE ALUMINOSILICATES AND THE USE OF CATALYST SO PRODUCED

[75] Inventors: William J. Ball, Capel; David G. Stewart, Epsom, both of England

[73] Assignee: The British Petroleum Company p.l.c., London, England

[21] Appl. No.: 578,426

[22] Filed: Mar. 27, 1984

Related U.S. Application Data

[62] Division of Ser. No. 396,361, Jul. 8, 1982, Pat. No. 4,452,908.

[30] Foreign Application Priority Data

Jul. 8, 1982 [GB] United Kingdom ............... 8122768
Jul. 8, 1982 [GB] United Kingdom ............... 8123619

[51] Int. Cl.$^3$ .................................................. C07C 3/10
[52] U.S. Cl. ...................................... 585/415; 585/533
[58] Field of Search ............... 502/61, 64; 585/415, 585/533

[56] References Cited

U.S. PATENT DOCUMENTS

| | | | |
|---|---|---|---|
| 3,213,013 | 10/1965 | Arey, Jr. | 502/74 |
| 3,264,208 | 8/1966 | Plank et al. | 208/120 |
| 3,360,484 | 12/1967 | Laurent | 502/79 |
| 3,509,042 | 4/1970 | Miale | 502/74 |
| 4,341,748 | 7/1982 | Plank et al. | 423/328 |
| 4,452,907 | 6/1984 | Ball et al. | 502/61 |
| 4,452,908 | 6/1984 | Ball et al. | 502/61 |

Primary Examiner—Delbert E. Gantz
Assistant Examiner—A. Pal
Attorney, Agent, or Firm—Brooks, Haidt, Haffner & Delahunty

[57] ABSTRACT

A process for the production of a catalyst based on a crystalline aluminosilicate having a silica to alumina molar ratio greater than 12:1 which is obtained by mixing a source of silica, a source of alumina, a source of alkali metal, water and a source of ammonium ions in defined proportions, crystallizing the mixture, recovering the crystalline aluminosilicate so-formed, cation-exchanging and/or impregnating the recovered crystalline aluminosilicate and finally calcining, wherein either the recovered crystalline aluminosilicate or the cation-exchanged aluminosilicate or the impregnated aluminosilicate is washed with a solution containing either an organic base, a carboxylic acid, an alcohol, a glycol, a phenol or an ester. The washing treatment results in a reduction in the rate of decline in catalytic activity in reactions such as the conversion of aliphatic to aromatic hydrocarbons.

1 Claim, No Drawings

PROCESS FOR THE PRODUCTION OF CATALYSTS BASED ON CRYSTALLINE ALUMINOSILICATES AND THE USE OF CATALYST SO PRODUCED

This is a division of application Ser. No. 396,361, filed July 8, 1982, now U.S. Pat. No. 4,452,908, issued June 5, 1984.

The present invention relates to a process for producing catalysts based on crystalline aluminosilicates having a silica to alumina molar ratio greater than 12:1 and their use.

In our copending European patent application publication No. 0030811 (BP Case No. 4896) there is described a process for the production of a crystalline aluminosilicate having a silica to alumina molar ratio greater than 12:1 by mixing a source of silica, a source of alumina, a source of alkali metal, water and a source of ammonium ions, and maintaining the mixture at elevated temperature for a period such that crystallisation occurs characterised in that a source of ammonium ions is employed in the absence of an alcohol or alkylene oxide and the source of silica, the source of alumina, the source of alkali metal, water and the source of ammonium ions are mixed in the molar proportions (expressed in the case of the silica and alumina sources in terms of the equivalent moles of the oxide, in the case of the alkali metal source in terms of the equivalent moles of the hydroxide [MOH] and in the case of the source of ammonium ions in terms of free ammonia):

$SiO_2:Al_2O_3$ greater than 12:1
$MOH:Al_2O_3$ in the range from 1:1 to 20:1
$SiO_2:NH_3$ in the range from 1:1 to 200:1, and
$H_2O:MOH$ in the range from 30:1 to 300:1

The use of the active hydrogen-form and the metal-exchanged and/or metal impregnated-form, hereinafter referred to as the metal treated-form, of the crystalline aluminosilicate so-prepared as catalyst in processes such as the conversion of an aliphatic hydrocarbon feedstock to aromatic hydrocarbons is described. The active hydrogen-form and the metal treated-form are suitably prepared from the crystalline aluminosilicate by methods known in the art.

The hydrogen-form and the metal treated-form of the crystalline aluminosilicates possess a very high initial activity as catalyst in processes such as the conversion of aliphatic hydrocarbons to aromatic hydrocarbons but can suffer from the disadvantage that their catalytic activity declines with time on stream.

We have now found that the decline in catalytic activity can be retarded by washing either the recovered crystalline aluminosilicate or the cation-exchanged form of the crystalline aluminosilicate or the metal impregnated aluminosilicate with a solution containing either an organic base, a carboxylic acid, an alcohol, a glycol, a phenol or an ester.

Accordingly the present invention provides a process for the production of a catalyst based on a crystalline aluminosilicate having a silica to alumina molar ratio greater than 12:1 which crystalline aluminosilicate is obtained by mixing a source of silica, a source of alumina, a source of alkali metal, water and a source of ammonium ions in the absence of an alcohol or an alkylene oxide in the molar proportions (expressed in the case of the silica and alumina sources in terms of the equivalent moles of the oxide, in the case of the alkali metal source in terms of the equivalent moles of the hydroxide [MOH] and in the case of the source of ammonium ions in terms of free ammonia):

$SiO_2:Al_2O_3$ greater than 12:1
$MOH:Al_2O_3$ in the range from 1:1 to 20:1
$SiO_2:NH_3$ in the range from 1:1 to 200:1, and
$H_2O:MOH$ in the range from 30:1 to 300:1, maintaining the mixture at elevated temperature for a period such that crystallisation occurs, recovering the crystalline aluminosilicate so-formed, cation-exchanging the recovered crystalline aluminosilicate with either $H^+$, $NH_4^+$ or metal cations and/or impregnating the recovered crystalline aluminosilicate with a solution of a metal compound and finally calcining the exchanged and/or impregnated crystalline aluminosilicate characterised in that either the recovered crystalline aluminosilicate or the cation-exchanged crystalline aluminosilicate or the metal impregnated crystalline aluminosilicate is washed with a solution containing either an organic base, a carboxylic acid, an alcohol, a glycol, a phenol or an ester.

Suitable sources of silica include, for example, sodium silicate, silica hydrosol, silica gel, silica sol and silicic acid. The preferred source of silica is an aqueous colloidal dispersion of silica particles. A suitable commercially available source of silica is LUDOX Colloidal Silica manufactured by Du Pont (LUDOX is a Registered Trade Mark).

Suitable sorces of alkali metal include alkali metal hydroxides and alkali metal oxides. Preferably the alkali metal is sodium.

The source of ammonium ions may be for example ammonium hydroxide or an ammonium salt such as the halide, nitrate, sulphate or carbonate. Ammonium hydroxide may be added as an aqueous solution or formed "in situ" by passing ammonia gas into the aqueous mixture. 35% w/w and 25% w/w aqueous ammonia solutions having specific gravities of 0.880 and 0.910 respectively at 20° C. are commercially available and may be used in the process of the invention, but aqueous solutions of other concentrations may also be used.

It will be appreciated that each source of silica, alumina, alkali metal and ammonium ion can be supplied by one or more initial reactants and then mixed together in any order. For example, sodium silicate is a source of both sodium and silica. Thus the source of alumina and the source of silica may be supplied in whole or in part by an aluminosilicate, which may be either crystalline or amorphous. A seed, that is a small portion of the desired crystalline product, may be introduced if so desired but it is an advantage of the present invention that the introduction of a seed is not necessary for the efficient performance of the invention.

The molar composition of the initial mixture is preferably as follows:
$SiO_2:Al_2O_3$ in the range from 20:1 to 50:1
$MOH:Al_2O_3$ in the range from 2:1 to 10:1
$SiO_2:NH_3$ in the range from 20:1 to 100:1
$H_2O:MOH$ in the range from 30:1 to 100:1

Even more preferably the molar composition of the initial mixture is as follows:
$SiO_2:Al_2O_3$ in the range from 25:1 to 45:1
$MOH:Al_2O_3$ in the range from 3:1 to 7:1
$SiO_2:NH_3$ in the range from 25:1 to 40:1
$H_2O:MOH$ in the range from 40:1 to 60:1

Conditions which effect the formation of the crystalline aluminosilicate may be, for example, a temperature in the range from 120° to 210° C., preferably from 135° to 190° C. and a pressure in the range from autogenous to 26 bar (400 psig), preferably from autogenous to 16 bar (240 psig). Suitably the pressure may be autogenous, that is the pressure generated within a closed vessel at the crystallisation temperature. Alternatively pressures within the aforesaid ranges above autogenous pressure may be employed. Pressures above autogenous pressure may be achieved for example by pressurising with a suitable gas, eg nitrogen. The mixture may suitably be maintained under these conditions for a time of at least 4 hours and preferably from 20 to 150 hours. Generally a time of about 48 hours will be found suitable though times up to and in excess of 7 days may be employed. Of course the time should not be so protracted that the crystalline aluminosilicate produced is converted to quartz.

The reaction may suitably be carried out in a closed vessel capable of withstanding the elevated pressures employed during the process. Furthermore the reaction mixture may be agitated during the formation of the aluminosilicate.

The crystalline aluminosilicate may suitably be recovered from the crystallisation mixture by filtration, though other methods of recovery, such as centrifugation, may be used if so desired. Further details of the process for preparing the crystalline aluminosilicate may be found in our European patent application publication No. 0030811.

The recovered crystalline aluminosilicate prepared in the aforesaid manner will invariably contain alkali metal, which is generally undesirable in catalytic applications. Thus it is preferred to reduce the alkali metal content of the aluminosilicate to less than 0.2% by weight, or for certain catalytic applications, such as in the dehydrocyclodimerisation of paraffins, to less than 0.02% by weight. This may be achieved by subjecting the aluminosilicate to one or more ion-exchanges with a solution containing $H^+$, $NH_4^+$ or metal cations. For example, the aluminosilicate may be ion-exchanged with a solution containing ammonium cations and thereafter calcined to produce the active hydrogen-form of the aluminosilicate. Suitable metals which may be incorporated by ion-exchange include one or more metals belonging to Groups IB, IIB, IIIA, IVA, VA or VIII of the Periodic Table of Elements as published by the Chemical Rubber Publishing Company. Examples of suitable metals include aluminium, copper, silver, zinc, gallium, indium, thallium, lead, antimony, bismuth, iron, cobalt, nickel, ruthenium, rhodium, palladium, iridium and platinum. Before ion-exchange it may be preferable to treat the aluminosilicate with a solution of an acid, eg an aqueous mineral acid. Furthermore it may be desirable to carry out the ion-exchange in several stages. Calcination between the first and second stages may be used as a means for reducing the number of exchanges required.

Alternatively, or in addition, the aforesaid metals may be incorporated by impregnation with a solution of a suitable compound or compounds. The compounds of the metals used are suitably those compounds which will decompose on heating to form the corresponding oxides and which are soluble in water, eg the nitrates or chlorides. The amount of the metal or metals incorporated whether by exchange, impregnation or both may suitably be in the range from 0.1 to 5.0% by weight, based on the weight of the crystalline aluminosilicate.

Calcination after exchange and/or impregnation may suitably be accomplished by heating the crystalline aluminosilicate in air at a temperature in the range 400° to 700° C. for a period of from 2 to 48 hours.

Washing with the solution of either an organic base, a carboxylic acid, an alcohol, a glycol, a phenol or an ester may be effected either on the recovered crystalline aluminosilicate, ie the material as recovered from the crystallisation mixture, or on the cation-exchanged crystalline aluminosilicate, ie the $H^+$, $NH_4^+$ or the metal cation-exchanged crystalline aluminosilicate, or on the metal impregnated crystalline aluminosilicate. Prior to washing the crystalline aluminosilicate may be partially dried. This may suitably be achieved by heating at a temperature in the range 100° to 150° C., eg 120° C., for up to 20 hours, eg 16 hours.

Suitable organic bases include amines, alkanolamines and tetraalkylammonium compounds. The amine may be a primary, secondary or tertiary aliphatic or aromatic amine such as for example methylamine, ethylamine, propylamine, diethylamine, dipropylamine, triethylamine, tripropylamine, benzylamine etc. The alkanolamine may suitably be a mono-, di- or trialkanolamine such as for example mono-, di- and triethanolamine or propanolamine. Suitable tetraalkylammonium compounds include tetramethyl-, tetraethyl-, tetrapropyl- and tetrabutylammonium hydroxides. The organic base may suitably comprise from 1 to 25 percent, preferably from 5 to 15 percent, by weight of the solution. In the case of less soluble organic bases it will be appreciated that lower concentrations within the aforesaid ranges are desirable in order to ensure a homogeneous solution.

Suitably the carboxylic acid may be an aliphatic or an aromatic carboxylic acid. Examples of suitable carboxylic acids which may be used in the process of the invention include formic acid, acetic acid, propionic acid, butyric acid and benzoic acid. The alcohol may suitably be a $C_1$ to $C_4$ alkanol, such as methanol. The glycol may suitably be, for example, ethylene glycol or propylene glycol. Suitably the phenol may be phenol itself or an alkyl phenol. The ester may suitably be an ester of an aliphatic or an aromatic carboxylic acid, such as for example methyl acetate. The carboxylic acid, alcohol, glycol, phenol or ester may suitably comprise from 2 to 20 percent, preferably from 5 to 15 percent, by weight of the solution. In the case of less soluble compounds it will be appreciated that lower concentrations within the aforesaid ranges are desirable in order to ensure a homogeneous solution.

The organic base, carboxylic acid, alcohol, glycol, phenol or ester are employed in the form of a solution in a suitable solvent. Suitable solvents include water and aromatic hydrocarbons such as benzene. Preferably the solvent is water.

The washing may be effected either at ambient or elevated temperatures.

The catalyst so-prepared may be used in the form of a fixed or a fluidised bed in, for example, aromatisation, disproportionation, isomerisation, alkylation, dehydrocyclodimerisation and methanol conversion reactions.

It is preferred to use the catalyst prepared in the manner hereinbefore described modified by exchange and/or impregnation with gallium or aluminium, preferably gallium, as a catalyst in the conversion of aliphatic hydrocarbons to aromatic hydrocarbons.

Thus according to another aspect of the present invention there is provided a process for the production of aromatic hydrocarbons which process comprises contacting at elevated temperature and in the vapour phase a $C_2$ to $C_{12}$ aliphatic hydrocarbon feedstock with a catalyst produced by the process as hereinbefore described in which aluminium or gallium is incorporated either by exchange or impregnation.

Preferably the catalyst incorporates gallium therein.

Conditions under which the process may be carried out are well known in the art and are described for example in our copending European application No. 81301022.0 (BP Case No 4951).

The invention will now be illustrated by reference to the following Examples and Comparison Tests. In the Examples reference will be made to the use of a gallium nitrate solution. This was prepared as follows:

Gallium metal, ex Alcoa (100 g, 99.99% pure) was dissolved in concentrated nitric acid (500 ml) by warming. 910 ammonia solution (280 ml) containing 25% wt/wt ammonia was then added dropwise until a white precipitate just formed. The solution was stirred for one hour and diluted to 2 liters by the addition of deionised water.

PREPARATION OF CATALYSTS

Comparison Test 1

Alumina, Laporte Type A (228 g) was dissolved in a solution of sodium hydroxide (447 g) in deionised water (3179 g) by warming. This solution was then added with stirring to Ludox silica sol Grade AS40 (10,047 g, containing 40% wt/wt silica) and 0.910 aqueous ammonia solution (153 ml, containing 25% wt/wt ammonia). The hydro-gel was allowed to stand for 30 minutes and then transferred to a 5 gallon autoclave and heated at 170° C. for 60 hours with stirring. The crystalline aluminosilicate was filtered off, washed with deionised water and dried at 120° C. It had a silica and aluminium content of 40.0 and 2.9% wt/wt respectively and an X-ray diffraction (XRD) pattern, after calcination at 500° C., as shown in Table 1. The XRD pattern is that of an MFI-type zeolite as defined in the Atlas of Zeolite Structure Types by W M Meier and D H Olson, published by the structure commission of the International Zeolite Association, 1978.

This is not an example of the process of the present invention because the crystalline aluminosilicate was not washed with a solution of an organic base.

Comparison Test 2

The crystalline aluminosilicate product of Comparison Test 1 (30 g) was heated at 80° C. with a 1 molar solution of ammonium chloride (300 ml) for one hour and then filtered. This operation was carried out twice. The solid was washed with deionised water (200 ml) and heated with the gallium nitrate solution (5.6 ml) and deionised water (225 ml) at 80° C. for one hour. The mixture was filtered and the filter-cake washed with deionised water (200 ml) and dried at 120° C. 20 g of this catalyst was mixed with Ludox silica, grade AS40 (12.5 g, containing 40% silica) and sufficient deionised water to form a thick paste and the whole was formed into 1/16 inch extrudate.

This is not an example of the process of the present invention because it did not involve the step of washing with a solution of an organic base.

EXAMPLE 1

The product of Comparison Test 1 (30 g) was suspended in a solution of diethanolamine (20 g) and deionised water (80 g) and the whole heated with stirring at 40° to 60° C. for one hour. The mixture was filtered and the filter-cake washed with deionised water (200 g) and calcined at 530° C. for 4 hours.

The catalyst was then processed as described in Comparison Test 2.

EXAMPLE 2

Example 1 was repeated except that the diethanolamine treatment was carried out at 20° C. instead of at 40° to 60° C.

EXAMPLE 3

Example 2 was repeated except that only 2 g of diethanolamine was used instead of 20 g.

EXAMPLE 4

Example 3 was repeated except that tetramethylammonium hydroxide was used in place of diethanolamine.

EXAMPLE 5

Example 3 was repeated except that tetrapropylammonium hydroxide was used in place of diethanolamine.

Comparison Test 3

This crystalline aluminosilicate was prepared as described for Comparison Test 1 except that the crystallisation was carried out at 140° C. for 96 hours. The XRD pattern of the material after calcination at 500° C. was similar to that shown in Table 1.

This is not an example of the process of the present invention because it did not involve washing with a solution of an organic base.

Comparison Test 4

The crystalline aluminosilicate product of Comparison Test 3 (600 g) was converted to the ammonium form by ion-exchanging with a one molar ammonium nitrate solution (4500 ml). This operation was repeated twice. The mixture was filtered and the filter cake washed with deionised water (2000 ml). The solid was suspended in a solution of gallium nitrate (112.5 ml) and deionised water (4500 ml) and refluxed for 2 hours. The mixture was filtered and the filter-cake washed with deionised water (2000 ml) and dried at 120° C.

20 g of this catalyst was mixed with Ludox silica, grade AS40 (12.5 g, containing 40% silica) and sufficient deionised water to form a thick paste and the whole was formed into 1/16 inch extrudate.

This is not an example of the process of the present invention because it did not involve washing with a solution of an organic base.

EXAMPLE 6

The procedure of Comparison Test 4 was repeated except that the dry gallium exchanged crystalline aluminosilicate (30 g) before mixing with silica was suspended in a solution of diethanolamine (20 g) and deionised water (80 g) and the whole stirred for one hour. The mixture was filtered and the solid washed with deionised water and dried at 120° C.

20 g of the dry powder was mixed with Ludox silica, grade AS40 (12.5 g, containing 40% silica) and sufficient water to form a thick paste and the whole was formed into 1/16 inch extrudate.

EXAMPLE 7

Crystalline aluminosilicate from Comparison Test 1 (30 g) was suspended in a solution of glacial acetic acid (20 g) and deionised water (80 g) and the whole stirred at room temperature for one hour. The mixture was filtered and the filter-cake washed with deionised water (200 g) and calcined at 530° C. for 4 hours.

The calcined, acetic acid-washed crystalline aluminosilicate was then processed as described in Comparison Test 2.

EXAMPLE 8

Crystalline aluminosilicate from Comparison Test 1 (30 g) was suspended in a solution of ethylene glycol (20 g) and deionised water (80 g) and the whole stirred at room temperature for one hour. The mixture was filtered and the filter-cake washed with deionised water (200 g) and calcined at 530° C. for 4 hours.

The calcined ethylene glycol-washed crystalline aluminosilicate was then processed as described in Comparison Test 2.

EXAMPLE 9

Crystalline aluminosilicate from Comparison Test 1 (30 g) was suspended in a solution of methanol (20 g) and deionised water (80 g) and the whole stirred at room temperature for one hour. The mixture was filtered and the filter-cake washed with deionised water (200 g) and calcined at 530° C. for 4 hours.

The calcined, methanol-washed crystalline aluminosilicate was then processed as described in Comparison Test 2.

Catalyst Testing

The catalysts of Comparison Tests 2 and 4 and Examples 1 to 9 were activated by calcining in air at 500° C. for 16 hours.

Comparison Test 5

A feed of propane was passed over the catalyst produced in Comparison Test 2 at a temperature of 550° C. and a contact time of 6 seconds (NTP).

EXAMPLE 10

Comparison Test 5 was repeated except that the catalyst produced in Comparison Test 2 was replaced by the catalyst produced in Example 1.

This is not an example illustrating the invention because the catalyst was not produced by the process of the invention.

EXAMPLE 11

Comparison Test 5 was repeated except that the catalyst produced in Comparison Test 2 was replaced by the catalyst produced in Example 2.

EXAMPLE 12

Comparison Test 5 was repeated except that the catalyst produced in Comparison Test 2 was replaced by the catalyst produced in Example 3.

EXAMPLE 13

Comparison Test 5 was repeated except that the catalyst produced in Comparison Test 2 was replaced by the catalyst produced in Example 4.

EXAMPLE 14

Comparison Test 5 was repeated except that the catalyst produced in Comparison Test 2 was replaced by the catalyst produced in Example 5.

Comparison Test 6

Comparison Test 5 was repeated except that the catalyst produced in Comparison Test 2 was replaced by the catalyst produced in Comparison Test 4.

This is not an example illustrating the invention because the catalyst was not produced by the process of the invention.

EXAMPLE 15

Comparison Test 5 was repeated except that the catalyst produced in Comparison Test 2 was replaced by the catalyst produced in Example 6.

The results of Comparison Tests 5 and 6 and Examples 10 to 15 are given in Table 2.

It can be seen from Table 2 that the decline in activity of catalysts prepared according to the present invention (Examples 10 to 15) in the conversion of propane to aromatics is markedly retarded when compared with catalysts prepared by a route not involving the step of washing with a solution of an organic base (Comparison Tests 5 and 6).

EXAMPLE 16

A feed of propane was passed over the catalyst produced in Example 7 at a temperature of 550° C. and a contact time of 6 seconds (NTP).

EXAMPLE 17

Example 16 was repeated except that the catalyst produced in Example 8 was used in place of the catalyst produced in Example 7.

EXAMPLE 18

Example 16 was repeated except that the catalyst produced in Example 9 was used in place of the catalyst produced in Example 7.

The results of Examples 16 to 18 are given in Table 3.

TABLE 1

| | XRD PATTERN | |
|---|---|---|
| 2-Theta | d(Å) | Relative intensities, I/Io |
| 4.96 | 17.823 | 4 |
| 5.11 | 17.312 | 5 |
| 5.14 | 17.181 | 5 |
| 7.09 | 12.462 | 6 |
| 7.96 | 11.104 | 100 |
| 8.87 | 9.973 | 55 |
| 9.11 | 9.713 | 17 |
| 11.94 | 7.416 | 5 |
| 13.23 | 6.693 | 7 |
| 13.96 | 6.344 | 11 |
| 14.83 | 5.976 | 14 |
| 15.56 | 5.695 | 10 |
| 15.94 | 5.560 | 12 |
| 16.67 | 5.319 | 5 |
| 17.70 | 5.012 | 5 |
| 17.85 | 4.971 | 6 |
| 19.19 | 4.603 | 6 |
| 19.28 | 4.358 | 9 |
| 20.09 | 4.253 | 11 |
| 22.25 | 3.996 | 6 |
| 23.14 | 3.844 | 89 |
| 23.35 | 3.811 | 64 |
| 23.79 | 3.741 | 34 |

TABLE 1-continued

XRD PATTERN

| 2-Theta | d(Å) | Relative intensities, I/Io |
|---|---|---|
| 23.95 | 3.716 | 42 |
| 24.45 | 3.641 | 29 |
| 24.81 | 3.590 | 4 |
| 25.64 | 3.475 | 8 |
| 25.94 | 3.435 | 13 |
| 26.28 | 3.391 | 11 |
| 26.67 | 3.343 | 9 |
| 26.97 | 3.307 | 10 |
| 27.44 | 3.251 | 4 |
| 29.33 | 3.046 | 10 |
| 29.96 | 2.983 | 11 |
| 30.06 | 2.971 | 11 |
| 30.39 | 2.941 | 6 |
| 32.80 | 2.731 | 4 |

TABLE 2

CATALYST TEST RESULTS
Reaction temperature = 550° C.
Contact time = 6 sec (NTP)

| Example | Catalyst | Hours on stream | Propane conversion (wt) | Aromatic yield wt |
|---|---|---|---|---|
| Comp Test 5 | Comp Test 2 | 1 | 85 | 52 |
|  |  | 6 | 33 | 17 |
| 10 | Example 1 | 1 | 86 | 52 |
|  |  | 7 | 57 | 37 |
| 11 | Example 2 | 1 | 88 | 57 |
|  |  | 7 | 64 | 40 |
| 12 | Example 3 | 1 | 83 | 52 |
|  |  | 6 | 64 | 38 |
| 13 | Example 4 | 1 | 70 | 44 |
|  |  | 7 | 52 | 34 |
| 14 | Example 5 | 1 | 78 | 52 |
|  |  | 7 | 62 | 42 |
| Comp Test 6 | Comp Test 4 | 2 | 80 | 41 |
|  |  | 6 | 17 | 6 |
| 15 | Example 6 | 2 | 77 | 43 |
|  |  | 7 | 43 | 23 |

In Table 2 the following definitions are used.

$$\text{Contact time} = \frac{(\text{Gross volume of catalyst}) \times (\text{Time})}{\text{Volume of material flowing at NTP}}$$

$$\text{Conversion} = \frac{\text{Weight of reactant consumed}}{\text{Weight of same reactant fed}} \times 100$$

$$\text{Yield} = \frac{\text{Weight of product appearing}}{\text{Weight of reactant fed}} \times 100$$

TABLE 3

Catalyst Test Results
Reaction temperature = 550° C.
Contact Time = 6 sec (NTP)

| Ex | Catalyst | Hours on stream | Propane conversion (% wt)[2] | Aromatics yield (% wt)[3] |
|---|---|---|---|---|
| Comp Test 5 | Comp Test 2 | 1 | 85 | 52 |
|  |  | 6 | 33 | 17 |
| 16 | Example 7 | 1 | 85 | 53 |
|  |  | 6 | 72 | 48 |
| 17 | Example 8 | 1 | 84 | 50 |
|  |  | 6 | 57 | 34 |
| 18 | Example 9 | 1 | 78 | 48 |
|  |  | 6 | 60 | 35 |

1. $\text{Contact time} = \frac{(\text{Gross volume of catalyst}) \times (\text{Time})}{\text{Volume of material flowing at NTP}}$ 2. $\text{Conversion} = \frac{\text{Weight of reactant consumed}}{\text{Weight of reactant fed}} \times 100$ 3. $\text{Yield} = \frac{\text{Weight of product appearing}}{\text{Weight of reactant fed}} \times 100$

We claim:

1. In a process for the production of aromatic hydrocarbons at elevated temperature and in the vapor phase by contacting a $C_2$ to $C_{12}$ aliphatic hydrocarbon feedstock with a catalyst, the improvement which comprises employing as the catalyst a crystalline aluminosilicate having a silica to alumina molar ratio greater than 12:1 which crystalline aluminosilicate is obtained by mixing a source of silica, a source of alumina, a source of alkali metal, water and a source of ammonium ions in the absence of an alcohol or an alkylene oxide in the molar proportions expressed in the case of the silica and alumina sources in terms of the equivalent moles of the oxide, in the case of the alkali metal source in terms of the equivalent moles of the hydroxide, MOH, and in the case of the source of ammonium ions in terms of free ammonia:

$SiO_2:Al_2O_3$ greater than 12:1

$MOH:Al_2O_3$ in the range from 1:1 to 20:1

$SiO_2:NH_3$ in the range from 1:1 to 200:1, and $H_2O:MOH$ in the range from 30:1 to 300:1, maintaining the mixture at elevated temperature for a period such that crystallisation occurs, recovering the crystalline aluminosilicate so-formed, cation-exchanging the recovered crystalline aluminosilicate with either gallium or aluminum cations and/or impregnating the recovered crystalline aluminosilicate with a solution of a gallium or aluminum compound and finally calcining the exchanged and/or impregnated crystalline aluminosilicate characterised in that either the recovered crystalline aluminosilicate or the cation-exchanged crystalline aluminosilicate or the metal impregnated crystalline aluminosilicate is washed with a solution containing either an organic base, a carboxylic acid, an alcohol, a glycol, a phenol or an ester.

* * * * *